US00PP13033P2

(12) United States Plant Patent
Bergman

(10) Patent No.: US PP13,033 P2
(45) Date of Patent: Oct. 1, 2002

(54) CHRYSANTHEMUM PLANT NAMED 'YOGAINESVILLE'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/955,842

(22) Filed: Sep. 20, 2001

(51) Int. Cl.[7] ..... A01H 5/00
(52) U.S. Cl. ..... Plt./288
(58) Field of Search ..... Plt./288

*Primary Examiner*—Bruce R. Campell
*Assistant Examiner*—Anne Marie Günberg
(74) *Attorney, Agent, or Firm*—C. A. Whealy

(57) ABSTRACT

A distinct cultivar of Chrysanthemum plant named 'Yogainesville', characterized by its uniform plant habit; strong and freely branching growth habit; dark green foliage; uniform and freely flowering habit; early flowering, eight-week response time; large decorative-type inflorescences that are about 11.4 cm in diameter; pure white-colored ray florets with emarginate apices; good postproduction longevity with plants maintaining good substance and color for about three to four weeks in an interior environment; and tolerance to high production temperatures.

2 Drawing Sheets

BACKGROUND OF THE INVENTION

The present Invention relates to a new and distinct cultivar of Chrysanthemum plant, botanically known as *Chrysanthemum×morifolium* and hereinafter referred to by the name 'Yogainesville'.

The new Chrysanthemum is a product of a planned breeding program conducted by the Inventor in Fort Myers, Fla. and Salinas, Calif. The objective of the breeding program is to create new potted Chrysanthemum cultivars that are suitable for year-round production with uniform plant growth habit, good vigor, desirable inflorescence form and floret colors, fast response time, and good postproduction longevity.

The new Chrysanthemum originated from a cross made by the Inventor in February, 1997, in Salinas, Calif., of a proprietary Chrysanthemum seedling selection identified as code number YB-4674, not patented, as the female, or seed, parent with a proprietary Chrysanthemum seedling selection identified as code number YB-5173, not patented, as the male, or pollen parent. The new Chrysanthemum was discovered and selected by the Inventor as a single flowering plant within the progeny of the stated cross grown in a controlled environment in Salinas, Calif. The selection of this plant was based on its uniform plant growth habit, desirable inflorescence form and floret colors, fast response time, and excellent postproduction longevity.

Asexual reproduction of the new Chrysanthemum by vegetative tip cuttings was first conducted in Fort Myers, Fla. in July, 1998. Asexual reproduction by cuttings has shown that the unique features of this new Chrysanthemum are stable and reproduced true to type in successive generations.

SUMMARY OF THE INVENTION

The cultivar Yogainesville has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yogainesville'. These characteristics in combination distinguish 'Yogainesville' as a new and distinct Chrysanthemum:

1. Uniform plant habit.
2. Strong and freely branching growth habit.
3. Dense dark green foliage.
4. Uniform and freely flowering habit.
5. Can be grown as a disbud or spray-type.
6. Early flowering, eight-week response time.
7. Large decorative-type inflorescences that are about 11.4 cm in diameter.
8. Pure white-colored ray florets with emarginate apices.
9. Good postproduction longevity with plants maintaining good substance and color for about three to four weeks in an interior environment.
10. Tolerant to high production temperatures.

Compared to plants of the female parent selection, plants of the new Chrysanthemum have purer white-colored ray florets.

Plants of the new Chrysanthemum differ primarily from plants of the male parent selection in ray floret coloration as plants of the new Chrysanthemum have white ray florets whereas plants of the female parent have yellow ray florets.

Plants of the new Chrysanthemum can be compared to plants of the cultivar Surf, disclosed in U.S. Plant Pat. No. 4,585. In side-by-side comparisons conducted by the Inventor in Salinas, Calif., plants of the new Chrysanthemum differed from plants of the cultivar Surf in the following characteristics:

1. Plants of the new Chrysanthemum were more vigorous and somewhat more upright than plants of the cultivar Surf.
2. Plants of the new Chrysanthemum had larger inflorescences than plants of the cultivar Surf.
3. Plants of the new Chrysanthemum flowered about five days earlier than plants of the cultivar Surf.

4. Ray floret color of plants of the new Chrysanthemum was purer white than ray floret color of plants of the cultivar Surf.

5. Plants of the new Chrysanthemum were more high temperature tolerant than plants of the cultivar Surf.

Plants of the new Chrysanthemum can also be compared to plants of the cultivar White Diamond, disclosed in U.S. Plant Pat. No. 8,059. In side-by-side comparisons conducted by the Inventor in Salinas, Calif., plants of the new Chrysanthemum differed from plants of the cultivar White Diamond in the following characteristics:

1. Plants of the new Chrysanthemum had a more upright growth habit than plants of the cultivar White Diamond.

2. Plants of the new Chrysanthemum had darker green foliage than plants of the cultivar White Diamond.

3. Ray floret color of plants of the new Chrysanthemum was pure white whereas ray floret color of plants of the cultivar White Diamond was ivory.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of a typical flowering plant of 'Yogainesville' grown as a disbud-type.

The photograph on the second sheet comprises a close-up view of typical inflorescences of 'Yogainesville' grown as a disbud-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the summer in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At the time of pinching, the photoinductive short day/long night treatments were started. Plants used for this description were grown as disbud-types. Measurements and numerical values represent averages of typical flowering plants.

Botanical classification: *Chrysanthemum×morifolium* cultivar Yogainesville.

Commercial classification: Decorative-type potted Chrysanthemum.

Parentage:

*Female, or seed, parent.*—Proprietary *Chrysanthemum×morifolium* seedling selection identified as code number YB-4674, not patented.

*Male, or pollen, parent.*—Proprietary *Chrysanthemum×morifolium* seedling selection identified as code number YB-5173, not patented.

Propagation:

*Type.*—Terminal tip cuttings.

*Time to initiate roots.*—About four days at 21° C.

*Time to produce a rooted cutting.*—About ten days at 21° C.

*Root description.*—White, fibrous.

*Rooting habit.*—Freely branching.

Plant description:

*Appearance.*—Herbaceous decorative-type potted Chrysanthemum that can be grown as a disbud or as a spray-type. Stems mostly upright and somewhat outwardly spreading; uniform crown. Very freely branching, about four or five lateral branches develop after removal of terminal apex (pinching); dense and full plants.

*Plant height.*—About 33 cm.

*Plant width.*—About 46 cm.

*Lateral branches* (*peduncles*).—Length: About 29 cm. Diameter: About 5 mm. Internode length: About 2.6 cm. Strength: Strong. Texture: Pubescent. Color: 146A.

*Foliage description.*—Arrangement: Alternate. Quantity of leaves per lateral stem: About 13 or 14. Length: About 9.3 cm. Width: About 6.8 cm. Apex: Cuspidate to mucronate. Base: Attenuate. Margin: Palmately lobed, sinuses between lateral lobes mostly divergent. Texture: Upper and lower surfaces with very fine pubescence; veins prominent on lower surface. Color: Young foliage, upper surface: Darker than 147A. Young foliage, lower surface: Darker than 147B. Mature foliage, upper surface: Close to 147A. Mature foliage, lower surface: Close to 147B. Venation, upper surface: Close to 146B to 146C. Venation, lower surface: 147B to 146B. Petiole length: About 2.5 cm. Petiole diameter: About 2.5 mm. Petiole color, upper and lower surfaces: Close to 146C.

Inflorescence description:

*Appearance.*—Decorative-type inflorescence form with elongated oblong-shaped ray florets. Inflorescences borne on terminals above foliage. Disk and ray florets arranged acropetally on a capitulum. Not fragrant. Can be grown as a disbud or spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about 46 to 50 days later when grown as a disbud-type and about 51 to 56 days later when grown as a spray-type.

*Postproduction longevity.*—Inflorescences maintain good color and substance for about three to four weeks in an interior environment.

*Quantity of inflorescences.*—Grown as a disbud-type, only one inflorescence, the terminal inflorescence, develops per lateral branch.

*Inflorescence bud.*—Height: About 5 mm. Diameter: About 7 mm. Color: Closest to 137A.

*Inflorescence size.*—Diameter: About 11.4 cm. Depth (height): About 3.5 cm. Diameter of disc: About 3 mm; inconspicuous. Receptacle diameter: About 1 cm.

*Ray florets.*—Shape: Elongated-oblong. Orientation: Initially upright, then perpendicular to peduncle. Aspect: Initially incurved, then slightly concave. Length: About 5.3 cm. Width: About 1.2 cm. Apex: Emarginate. Base: Attenuate. Corolla tube length: About 1.7 cm. Margin: Entire. Texture: Smooth, glabrous, satiny. Number of ray florets per inflorescence: More than 250 arranged in numerous rows. Color: When opening and fully expanded, upper surface: Closest to 155D. When opening and fully expanded, lower surface: Closest to 155D.

*Disc florets.*—Arrangement: Massed at center of receptacle. Shape: Tubular, elongated. Apex: Five-pointed. Length: About 6 mm. Width: Apex: About 1 mm. Base: About 1 mm. Number of disc florets per inflorescence: Less than 5. Color: Immature: 154A. Mature: Apex: 7A. Mid-section and base: Closest to 155D.

*Reproductive organs.*—Androecium: Present on disc florets only. Anther color: 9A. Pollen: None observed. Gynoecium: Present on both ray and disc florets.

*Seed.*—Seed production has not been observed.

Disease resistance: Resistance to pathogens common to Chrysanthemums has not been observed on plants grown under commercial greenhouse conditions.

High temperature tolerance: Plants of the new Chrysanthemum have been observed to be tolerant to high temperature conditions when grown during the summer under greenhouse conditions in southwest Florida.

It is claimed:

1. A new and distinct cultivar of Chrysanthemum plant named 'Yogainesville', as illustrated and described.

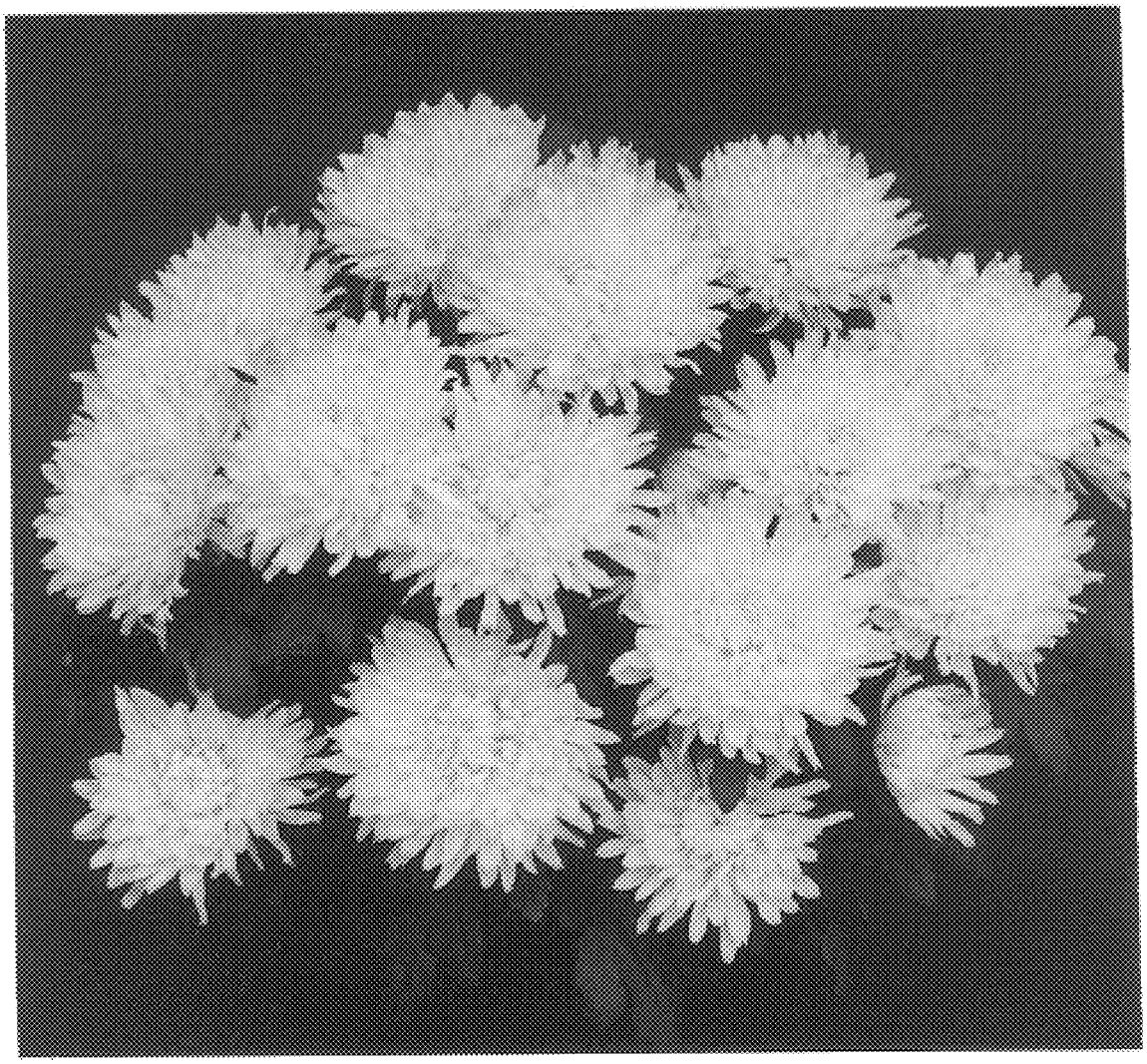

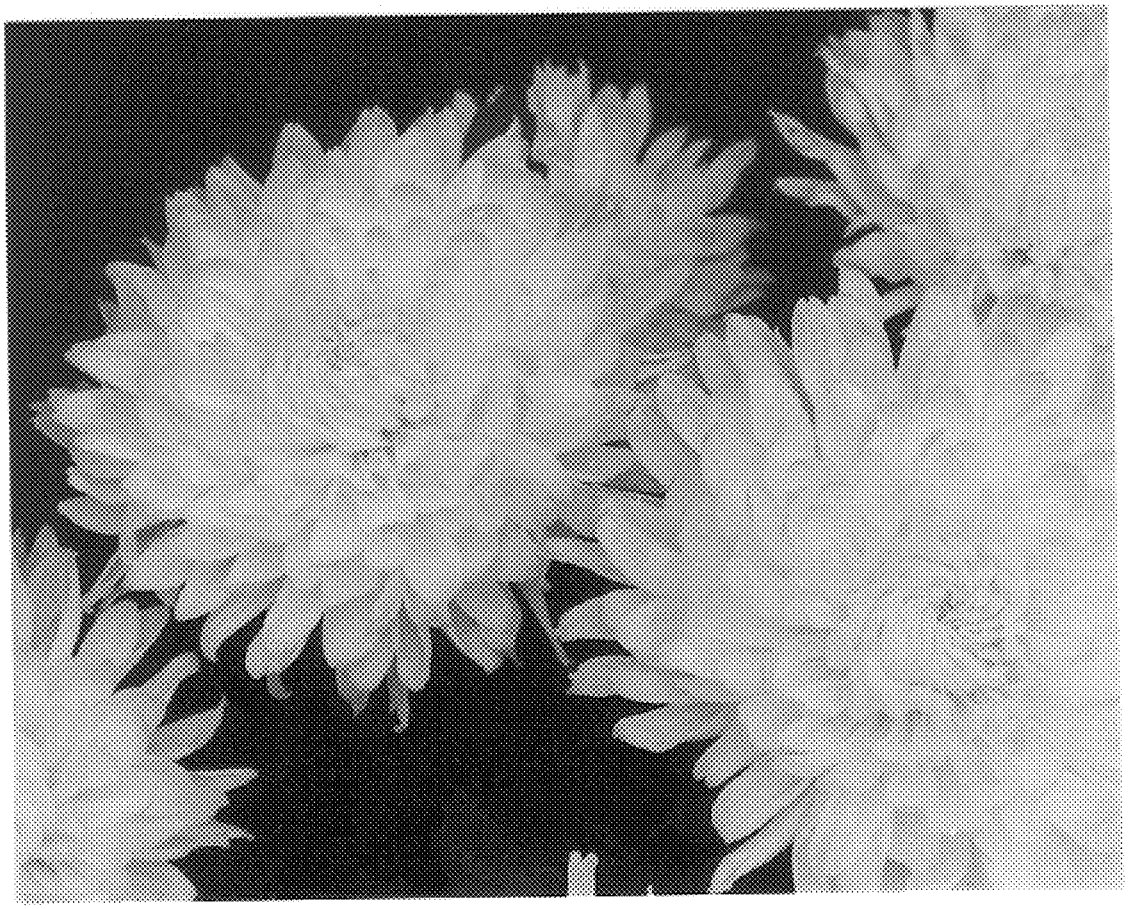

* * * * *